United States Patent [19]

Longenecker et al.

[11] Patent Number: 4,994,439

[45] Date of Patent: Feb. 19, 1991

[54] TRANSMEMBRANE FORMULATIONS FOR DRUG ADMINISTRATION

[75] Inventors: John P. Longenecker, Mountain View; Richard Ennis, Fremont; Patricia A. Baldwin, Hayward; William A. Lee, Los Altos, all of Calif.

[73] Assignee: California Biotechnology Inc., Mountain View, Calif.

[21] Appl. No.: 299,881

[22] Filed: Jan. 19, 1989

[51] Int. Cl.$^5$ .................. A61K 9/08; A61K 9/10; A61K 9/12; A61K 37/02

[52] U.S. Cl. ............................. 514/3; 424/45; 514/2; 514/171; 514/808; 514/922; 514/947; 514/958; 514/975

[58] Field of Search .............. 514/23, 975, 947, 958, 514/171, 866, 922, 808; 424/45

[56] References Cited

U.S. PATENT DOCUMENTS

| | | | |
|---|---|---|---|
| 3,230,240 | 1/1966 | Godtfredsen et al. | |
| 3,867,413 | 2/1975 | Daehne et al. | |
| 3,920,817 | 11/1975 | Godtfredsen | 424/242 |
| 4,100,276 | 7/1978 | von Daehne et al. | |
| 4,119,717 | 10/1978 | von Daehne et al. | |
| 4,153,689 | 5/1979 | Hirai et al. | |
| 4,323,558 | 4/1982 | Nelson | 424/164 |
| 4,372,888 | 2/1983 | Hjelmeland | |
| 4,537,776 | 8/1985 | Cooper | 514/424 |
| 4,548,922 | 10/1985 | Carey et al. | |
| 4,557,934 | 10/1985 | Cooper | 424/128 |
| 4,746,508 | 5/1988 | Carey et al. | 424/88 |
| 4,752,425 | 6/1988 | Martin et al. | 264/4.6 |
| 4,789,660 | 12/1988 | Enever et al. | 514/4 |

FOREIGN PATENT DOCUMENTS

| | | | |
|---|---|---|---|
| 0046523 | 3/1982 | European Pat. Off. | |
| 0111841 | 6/1984 | European Pat. Off. | |
| 0200383 | 12/1986 | European Pat. Off. | 514/958 |
| 0257956 | 3/1988 | European Pat. Off. | 514/958 |
| 360340 | 3/1990 | European Pat. Off. | |
| 261096 | 10/1988 | German Democratic Rep. | 514/958 |
| 60-161924 | 8/1985 | Japan | 514/958 |
| 63-211237 | 9/1988 | Japan | 514/958 |
| 8707504 | 12/1987 | PCT Int'l Appl. | 514/958 |
| 8800829 | 2/1988 | PCT Int'l Appl. | 514/958 |
| 8801864 | 3/1988 | PCT Int'l Appl. | 514/958 |
| 1527605 | 8/1975 | United Kingdom | |
| 2127689 | 10/1983 | United Kingdom | |
| 2193891 | 2/1988 | United Kingdom | 514/958 |

OTHER PUBLICATIONS

Longenecker et al., C.A. 107: 83791k (1987).
Duchateau et al. C.A. 107: 242511n (1987).
Su et al. C.A. 106: 162571w (1986) of EP 200383, Dec. 10, 1986.
Veda et al. C. G. 104: 10621h (1986) of JP 60/16192y, Aug. 23, 1985.
Martin et al. C. A. 110: 121402f (1989) of PCT WO88/01864, Mar. 24, 1988.
G. S. M. J. E. Duchateu et al., *Int. J. Pharm.* 39: 87–92 (1987).
J. P. Longenecker et al., *J. Pharm. Sci.:* 351–355 (1987).
W. A. Lee et al., "Intranasal Bioavailability of Insulin Powder Formulations . . ." submitted to *J. Pharm. Sci.*, in press.
R. D. Ennis et al., *Pharm. Res.* 7 (5): 468–475 (1990).
Carey et al., *Biochem.* (1975) 22(14): 4896–4904.
Carey et al., *J. Lipid Res.* (1971) 12: 605–613.
Carey et al., "Bile Acids In Gastroenterology" (1983), pp. 19–56.
Deuxchaisnes et al., "Effect of a Nasal Spray of Slamon Calcitonin in Normal Subjects and in Patients with Paget's Disease of Bone", Elsevier Science Publishers BV, A. Pecile, Editor, pp. 329–343.

(List continued on next page.)

*Primary Examiner*—Shep K. Rose
*Attorney, Agent, or Firm*—Irell & Manella

[57] ABSTRACT

Compositions for the administration of protein or peptide drugs across membranes show low toxicity and efficient permeation when the medium is a mixture of a bile salt or fusidate with a nonionic detergent. Various specific compositions are exemplified.

23 Claims, 8 Drawing Sheets

OTHER PUBLICATIONS

Deuxchaisnes et al., *British Med J.* (1985) 291: 544–545.
Gordon et al., *Proc. Natl. Acad. Sci.* (1985) 82: 7419–7423.
Hjelmeland et al., *Analytical Biochem.* (1983) 130: 72–82.
Kiebzak et al., *Gen. and Compar. Endocrinol.* (1982) 48: 232–238.
Morimoto et al., *J. Pharmaceutical Sci.* (1984) 72(10): 1366–1368.
Muranishi, *Meth. and Find. Exptl. Clin. Pharmacol.* (1984) 6(12):763–772.
Ziegler et al., *Acta Endocrin. Suppl.* (1978) 215: 54–55.

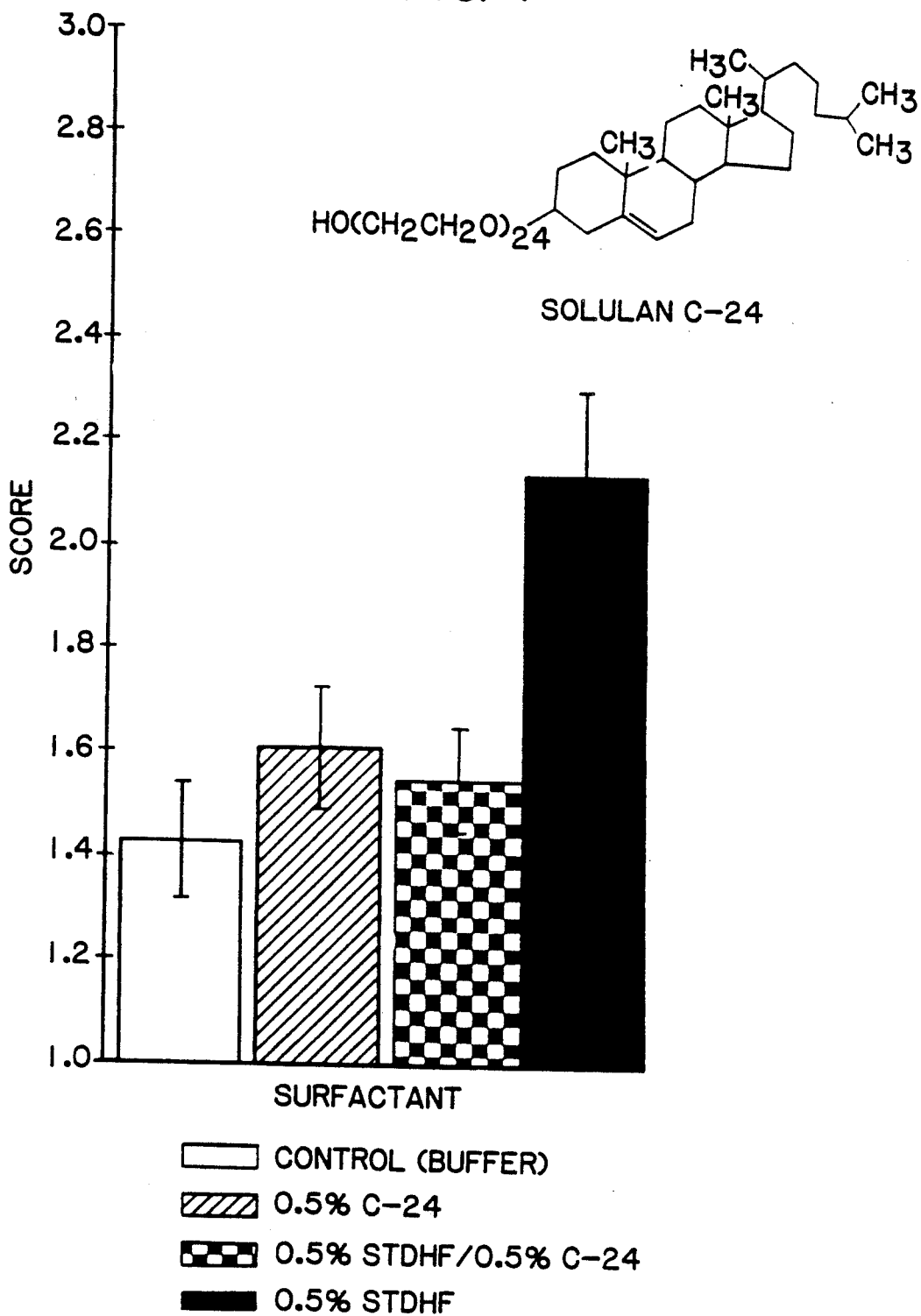

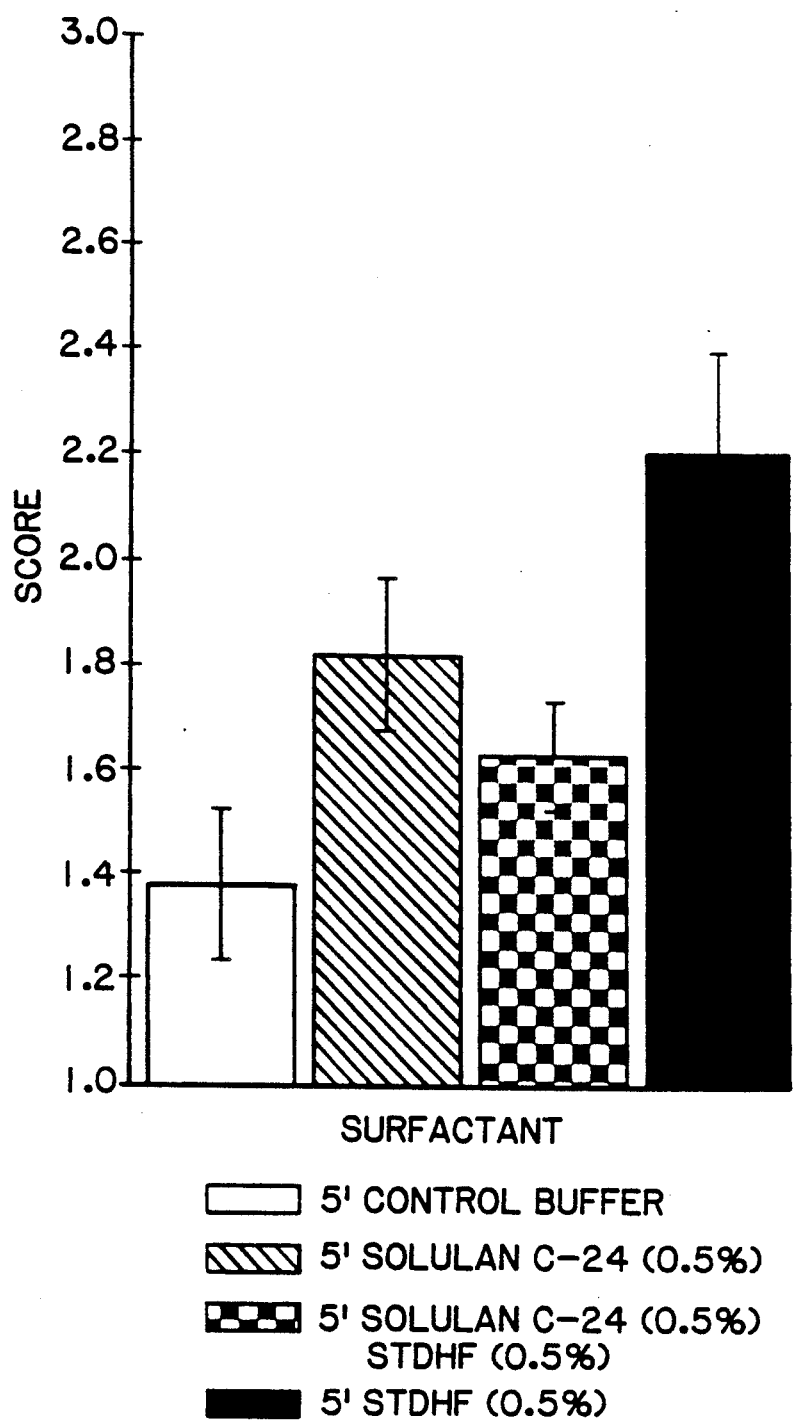

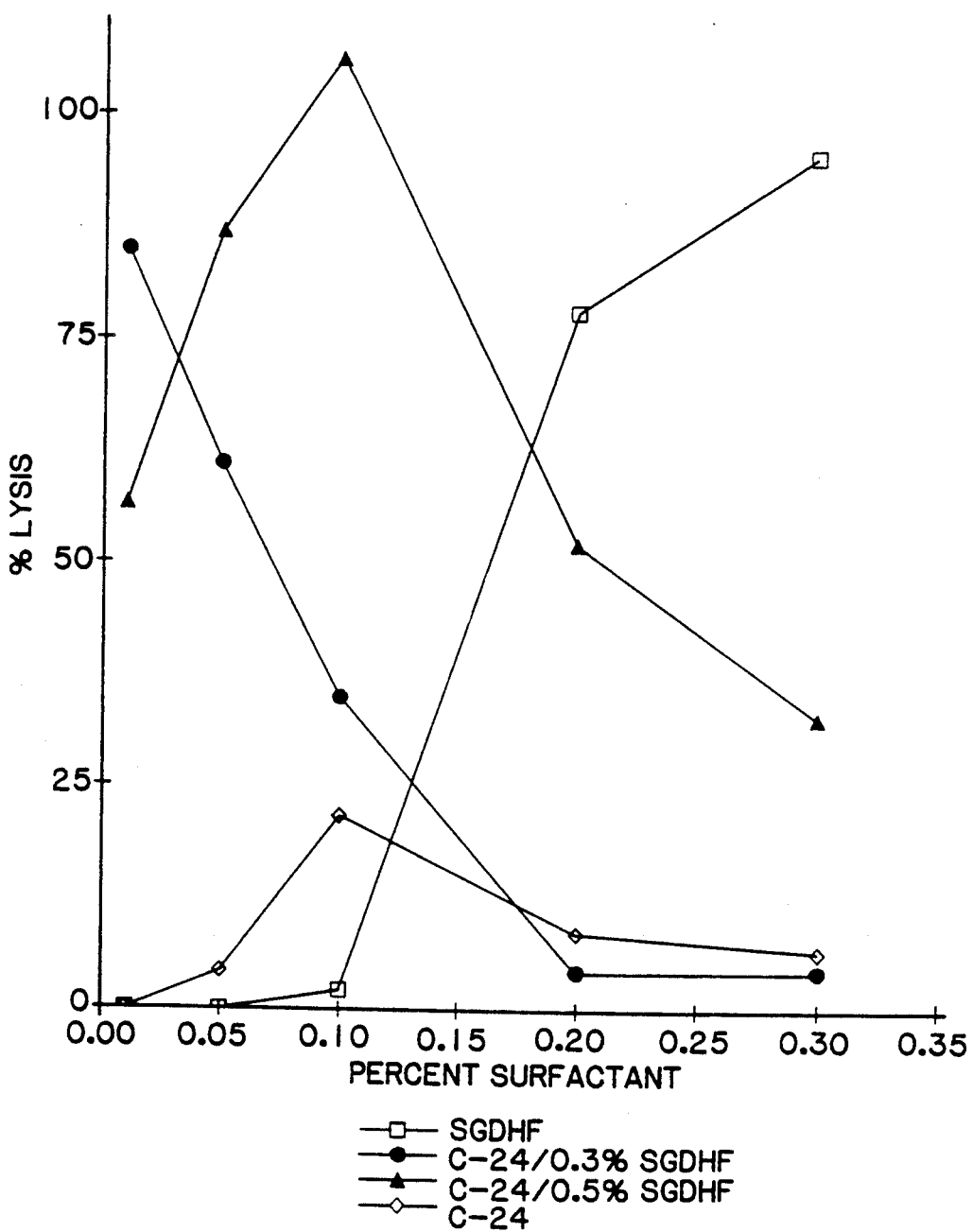

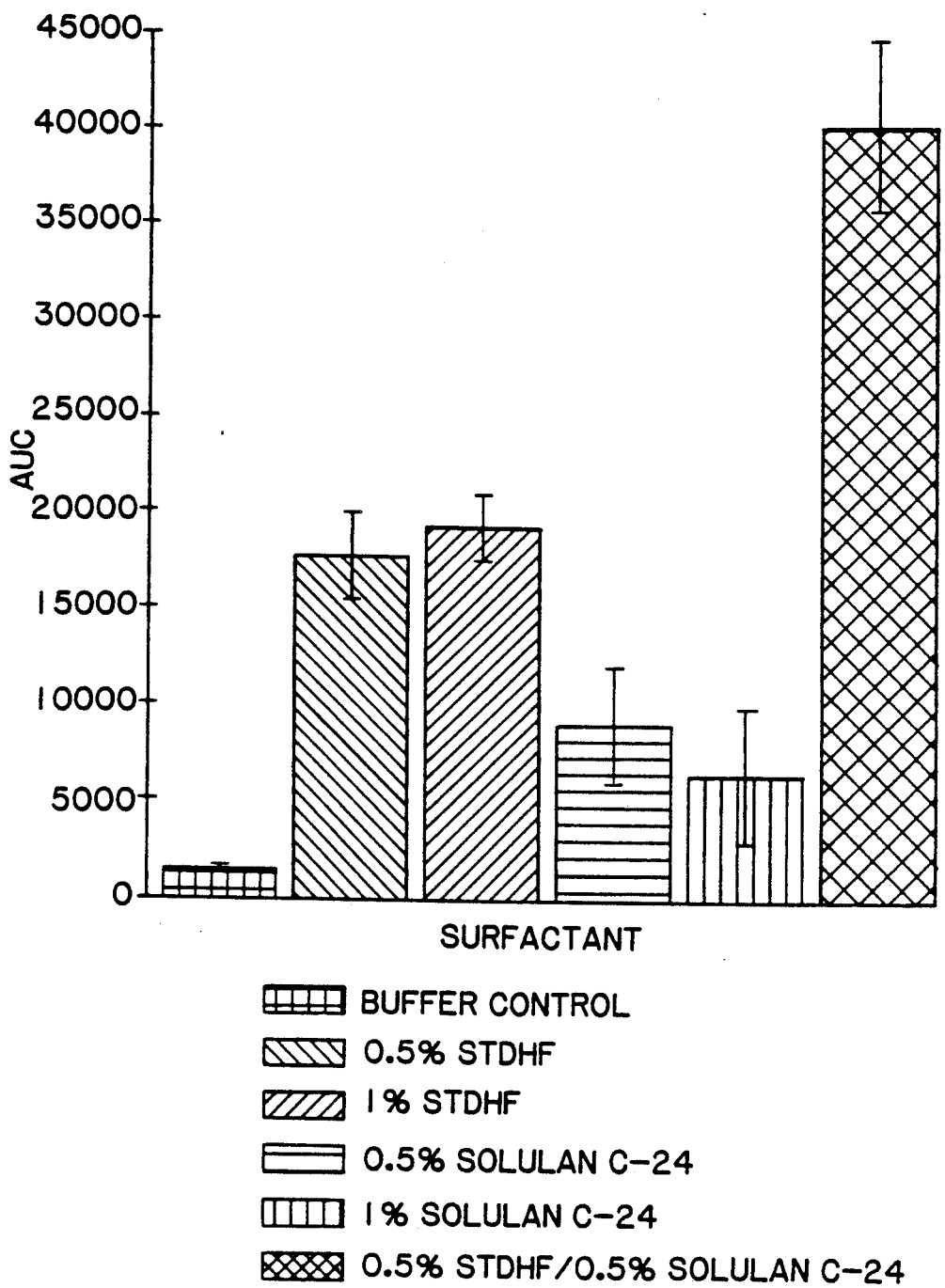

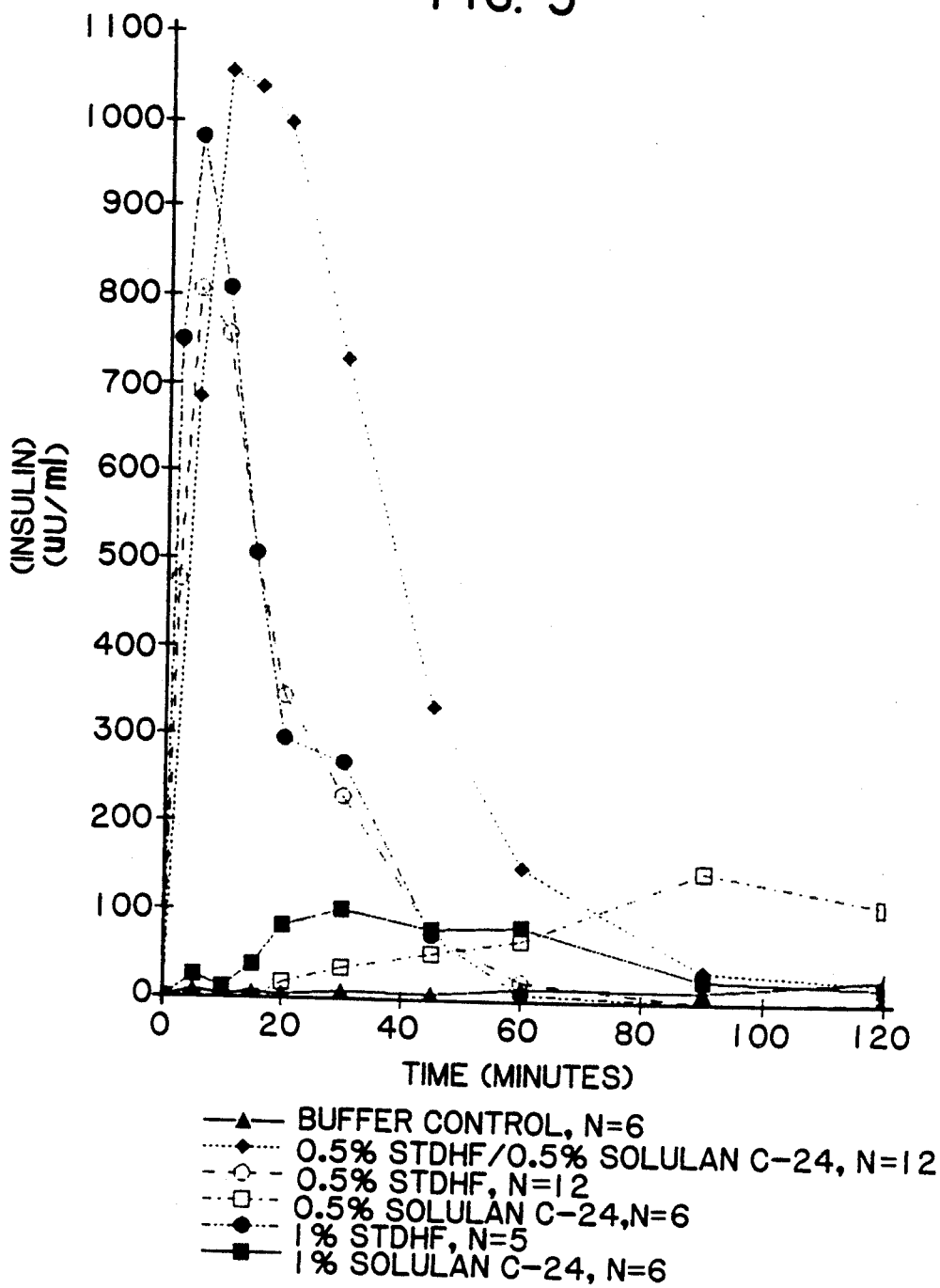

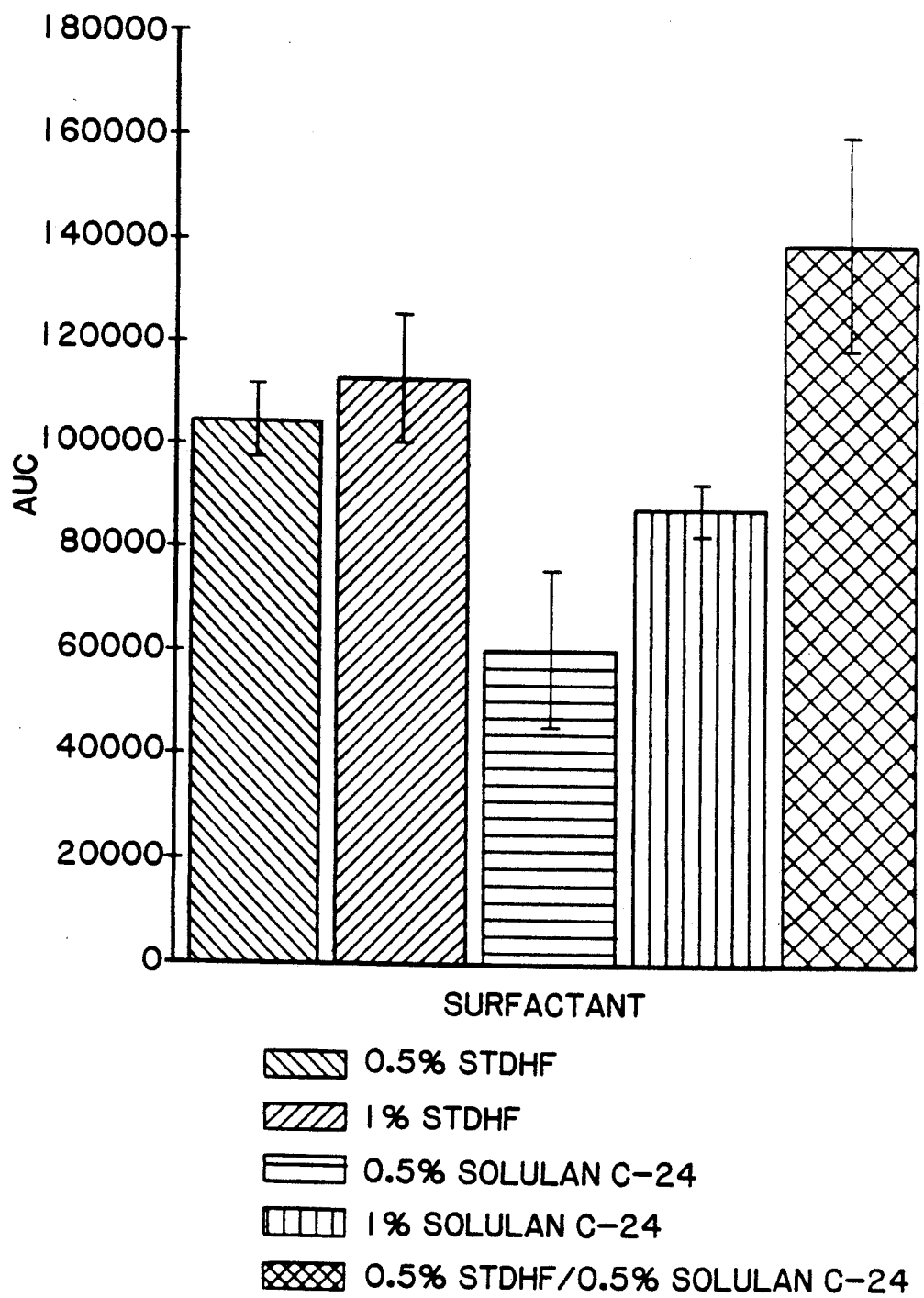

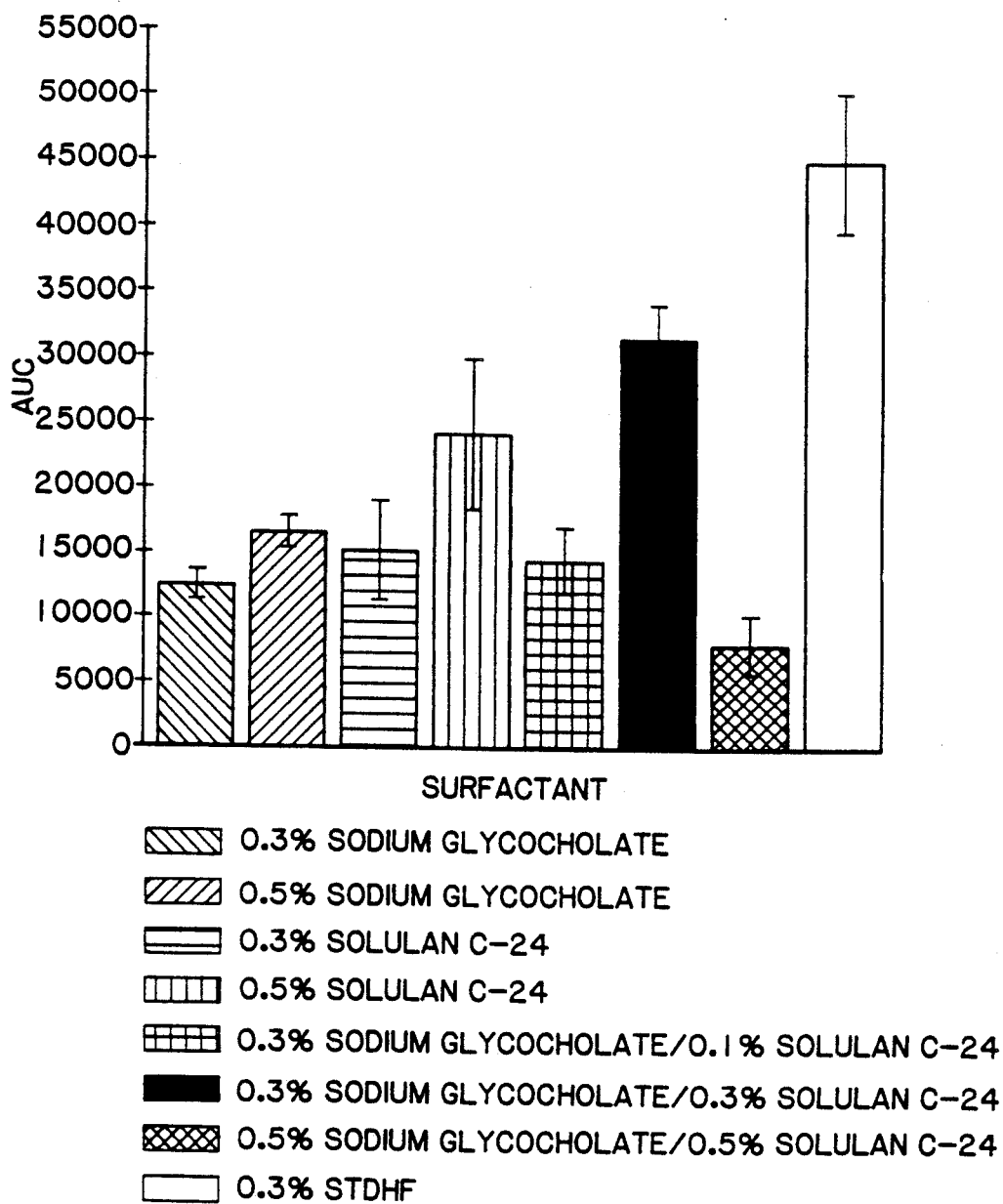

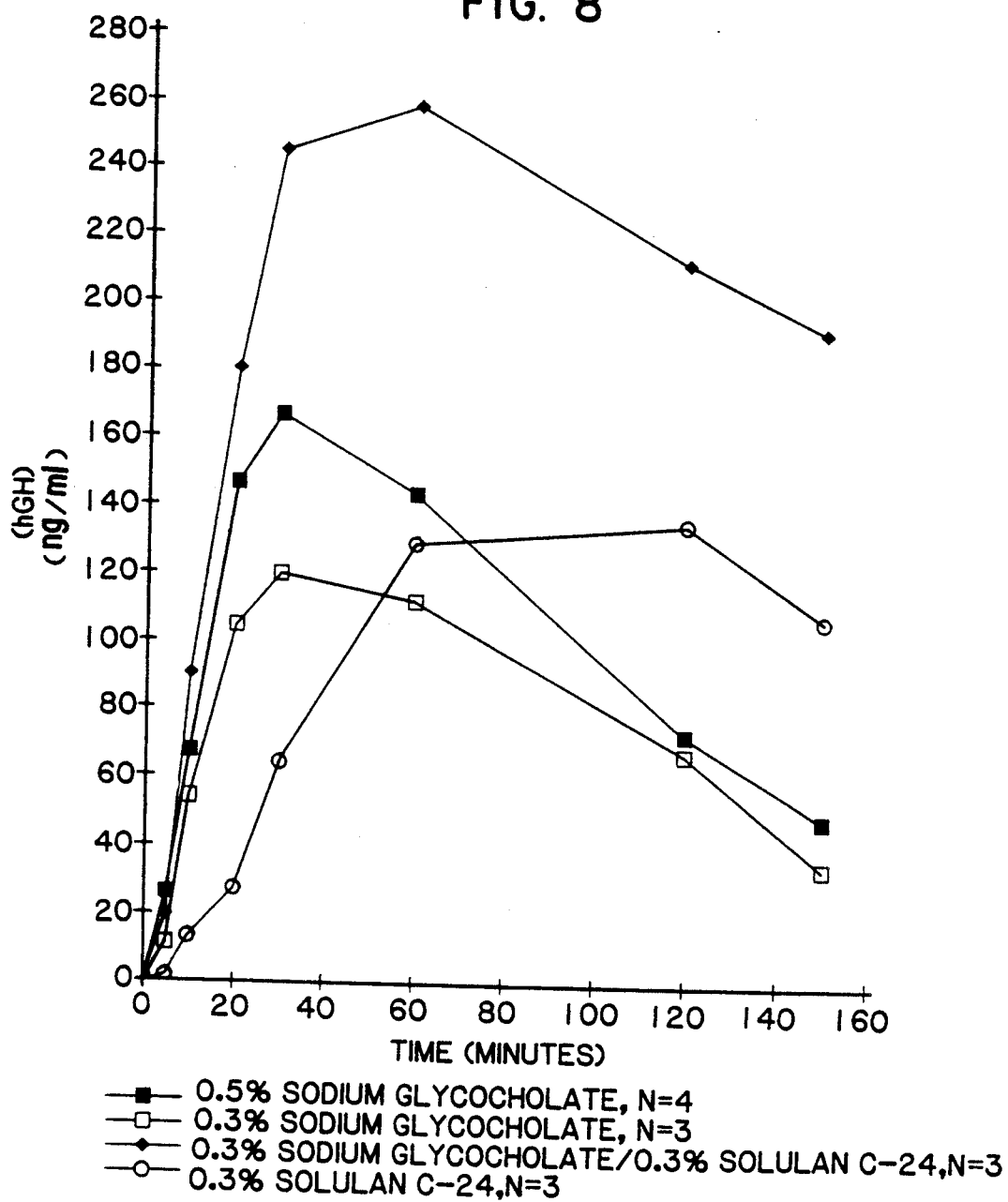

TRANSMEMBRANE FORMULATIONS FOR DRUG ADMINISTRATION

TECHNICAL FIELD

The invention relates to the administration of drugs using compositions containing the drugs with carriers suitable for transport across mucosal membranes. In typical embodiments, the invention employs pharmaceutical compositions which are capable of permeating the nasal membranes on account of the properties of the carrier. The carriers of the invention are mixtures of nonionic detergents and bile salts or fusidates, and their derivatives.

BACKGROUND ART

Pharmaceutical compositions which contain peptides or proteins as active ingredients present difficulties for oral administration since the active ingredients are attacked by the digestive system. Because oral administration is therefore tricky, and administration by injection is uncomfortable and presents a psychological barrier as well as some physiological risk, alternative means to administer these drugs have been sought.

Transfer of the drugs across a dermal layer or a mucosal membrane has been attempted. Transdermal administration is generally and logically fairly difficult as the function of the skin is to exclude substances from the interior of the organism. On the other hand, mucosal membranes are adapted to some level of absorption. Mucosal membranes are found, generally, in the digestive tract and in the respiratory system. It has therefore been possible in some instances to use either suppositories or nasal sprays as a method to deliver drugs systemically.

It is by now well known that bile salts are capable of enhancing the absorption of peptides, such as insulin and other drugs, across the nasal mucous membrane and across the rectal and vaginal mucous membranes (Duchateau, G.S.M.J.E. et al, in "Studies on Nasal Drug Delivery" (1986) Thesis:University of Amsterdam, pp. 87–98, citing Collens, W.S. et al, Proc Soc Exp Biol & Med (1932) 29:756–758; Toultou, E., et al, J Pharm Pharmacol (1978) 30:662–663 and a variety of other references). More recently, it has been shown that compositions containing a biocompatible, water soluble, amphiphilic steroid such as a fusidic acid derivative or a cephalosporin P derivative are also thus effective (Carey et al, U.S. Pat. No. 4,548,922 issued 22 Oct. 1985).

The use of nonionic detergents as carriers for the transmucosal administration of various drugs is also known. For example, British patent No. 2,127,689 to Sandoz claims a calcitonin composition which relies, for its ability to transport the active ingredient across the mucosal membrane, on an effective amount of a nonionic detergent which is a polyalkylene oxide derivative. In addition, polyacrylic acid gels have been used for nasal absorption of insulin and calcitonin by Morimoto, K., et al, J Pharm Pharmacol (1985) 37:134–136. U.S. Pat. No.4,153,689, assigned to Takeda describes an insulin nasal composition using Tween or polyoxyethylene-9-lauryl ether.

Sporadic reports of mixtures of carrier materials have also appeared. Muranishi, S., in Pharmaceutical Research (1985) pp. 108–118 describes monolein/bile salt mixed micelles as carriers which enhance the intestinal absorption of heparin. Oleic acid is also disclosed as useful in combination with a bile salt.

British Patent No. 1,527,605 to Takeda describes nasal administration of insulin with an adjuvant which is either a polyoxyethylene-9-lauryl ether or sodium glycocholate. While the specification casually indicates that mixtures of these excipients may be used, mixtures are not exemplified, nor is it clear what mixtures the disclosure intends to encompass. In addition, EPO Publication No. 0111847 to Syntex discloses the use of polysorbates mixed with bile salts for the administration of LHRH. Again, the specific features of this mixture are not identified, and the focus of the disclosure is on the utility of the bile salt.

Thus, although the use of bile salts with other detergents has been alluded to in these references in a general way, the inclusion of these additional surfactants in the carrier has been proposed as the inclusion of a harmless ingredient rather than a component which would change the characteristics (for better or worse) or the permeation capabilities of the bile salt composition with respect to the drug. To Applicants' knowledge there are no disclosures at all of administration of drugs using fusidates in admixture with nonionic detergents.

It has now been found that mixtures of bile salts or fusidates or their derivatives with nonionic detergents which are related to polymerized alkylene glycols or oxides provide compositions which have equivalent or increased permeation ability and lower toxicity compared to compositions containing corresponding amounts of bile salt or fusidate excipient alone.

DISCLOSURE OF THE INVENTION

The invention provides drug administration compositions with the ability to transport peptide, protein, or other drugs across mucous membranes with efficiencies comparable to or better than those achieved using bile salts/fusidates alone but with a better safety profile than those associated with compositions containing only these excipients. While certain detergents, such as Solulan C-24, are not very deleterious to mucous membranes, they are poor absorption promoters. The carrier portions of the compositions utilize the combination of either bile salts or fusidates or their derivatives with nonionic detergents. The nonionic detergents are hydrophobic ether derivatives of polymerized alkylene glycols or epoxides.

Thus, in one aspect, the invention is directed to compositions for transmucosal administration of drugs which compositions comprise, in addition to the active ingredient, effective mixtures of one or more bile salts or fusidates or derivatives thereof with one or more nonionic detergents of the formula $RO(CHR'CH_2O)_nR$ wherein n is 1–150, and one R is H and the other is a saturated or unsaturated cyclic or acyclic organic residue of 6–40 carbon atoms. The non-H R is generally the radical portion of a sterol or of lauryl or other long-chain alcohol. The mixture of carrier components results in the formation of mixed micelles; thus the concentration of carrier must be above the critical micellar concentration (CMC) for the combination. The weight ratio of bile salt/fusidate/ derivative to nonionic surfactant can be fairly broad—about 10:1 to 1:10.

In another aspect, the invention relates to methods to administer drugs using the compositions herein.

BRIEF DESCRIPTION OF THE DRAWINGS

FIG. 1 shows the effect of Solulan C-24 (C-24) and sodium tauro-24,25-dihydrofusidate (STDHF) singly and in combination on rat mucosal surface integrity.

FIG. 2 shows similar data as measured by rat ciliary morphology.

FIG. 3 shows the effect of addition of detergent to fusidate preparations on lysis of red blood cells.

FIG. 4 shows the ability of STDHF to effect transport of insulin when combined with Solulan C-24 in various percentages.

FIG. 5 shows the time course of insulin concentration in the blood when administered using STDHF alone or mixtures with Solulan C-24.

FIG. 6 shows a comparison of the amount of human growth hormone transported into the blood stream using STDHF or Solulan C-24 alone or in combination.

FIG. 7 shows similar data for combination of sodium glycocholate and Solulan C-24.

FIG. 8 shows the time course of human growth hormone levels in the blood when the hormone is administered using sodium glycocholate and Solulan C-24 alone or together.

MODES OF CARRYING OUT THE INVENTION

The invention is directed to pharmaceutical compositions suitable for effecting the transport of a drug or pharmaceutical, including a peptide/protein drug across a mucous membrane.

As used herein, "pharmaceutical" or "drug" refers to a substance useful for the treatment of or the prevention of a human or animal disorder or in the regulation of a human or animal physiological condition or metabolic state.

As used herein, "peptide/protein drug" refers to pharmaceuticals whose active portion constitutes an amino acid sequence of varying length from about 5–10 amino acids to very large proteins of about 300 kd. The protein portion may also contain additional derivatizing groups such as sugars or lipids. The invention permits the administration of the peptide/protein drugs without direct injection, as would be the case for intramuscular, subcutaneous, or intravenous administration. This transmembrane route, while associated with some degradation of the peptide, results in much less hydrolysis than that encountered in oral administration.

Suitable peptide/protein drugs are exemplified by, for example, insulin, proinsulin, glucagon, parathyroid hormone, calcitonin, vasopressin, renin, prolactin, growth hormone, thyroid-stimulating hormone, corticotropin, follicle-stimulating hormone, luteinizing hormone, chorionic gonadotropin, CGRP, atrial peptides, interferon, tissue plasminogen activator, gamma-globulin, factor VIII, urokinase, streptokinase, the various lymphokines such as interleukin-2, colony stimulating factors, and so forth. As is well known, modifications of the native amino acid sequences of the foregoing proteins and fragments thereof may also be used as agonists or antagonists for the native peptides. Further examples of native proteins for which altered or fragmented agonists or antagonists are available include growth hormone releasing factor, corticotropin releasing factor, luteinizing hormone releasing hormone (LHRH), somatostatin, calcitonin, thyrotropin releasing hormone, calcitonin gene related peptide (CGRP), and other proteins such as enzymes, including transferases, hydrolases, isomerases, proteases, ligases, oxidoreductases, esterases, phosphatases, and various growth factors such as nerve growth factor, epidermal growth factor, fibroblast growth factor, insulin-like growth factor, and TGF-beta. Other proteins include vaccines derivable from the proteins of viral and bacterial and parasitic infective agents.

In addition to peptide/protein drugs and pharmaceuticals, other active ingredients can also be administered using the transmucosal membrane compositions of the invention. While these drugs are often capable of oral administration, transmucosal treatment may be desirable for a variety of reasons, including uniformity of dosage when protein/peptide drugs must also be administered, problems with digestion of the material itself, or the capacity of the drug to irritate the digestive tract.

An exemplary, but not all inclusive, list of additional drugs which can be administered using the composition of the invention would comprise antihistamines, e.g. diphenhydramine and chlorphenirmine, and drugs affecting the cardiovascular, renal, hepatic and immune systems, such as antihypertensives, beta blockers, and cholesterol lowering agents; sympathomimetic drugs, such as the catecholamines, e.g. epinephrines; noncatecholamines, e.g. phenylephrine and pseudoephedrine; anti-infective agents, including antibacterial, antiviral and antifungal agents, such as the aminoglycosides, e.g., streptomycin, gentamicin, kanamycin; anti-arthritis drugs, such as narcotic pain relievers; anti-inflammatory agents, e.g. indomethacin, dexamethasone and triamcinolone; antitumor agents, e.g. 5-fluorouracil and methotrexate; tranquilizers, such as diazepam; water insoluble, fat-soluble hydrophobic drugs, e.g. steroids such as progesterone, estrogens, including contraceptives such as ethinyl estradiol and androgens and their analogs, and the fat-soluble vitamins, e.g. vitamins A, D, E and K, and their analogs.

The carrier portion of the pharmaceutical compositions is comprised of the bile salt or fusidate or derivative thereof as one type of component in combination with the nonionic surfactant in a ratio of 10:1 to 1:10 by weight.

As used herein, "bile salts" refers to the group of steroids produced by the liver as bile. In humans, the primary bile acids are cholic acid and chenodeoxycholic acid. These steroids and their derivatives are the major components of the bile. Some of these primary bile acids are derivatized to glycine or taurine to form glycocholic and taurocholic acids and glycochendeoxycholic and taurochendeoxycholic acids. These cholic and chenodeoxycholic acid derivatives of the primary bile products can be deoxygenated at C-7 to form the secondary deoxycholic, glycodeoxycholic, taurodeoxycholic and lithocholic, glycolithocholic and taurolithocholic acids. The primary bile acid structures, cholic acid and chenodeoxycholic acid are

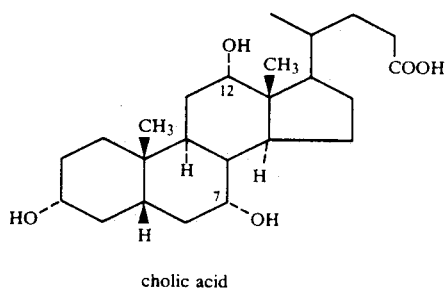

cholic acid

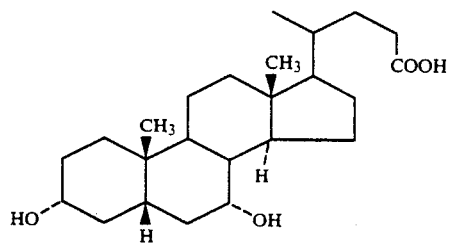

chenodeoxycholic acid wherein the carboxyl qroup on the side chain can be combined in a peptide linkage with either glycine or taurine. The secondary bile products lack the OH at C7.

However, modifications of these basic structures, specifically those wherein the peptide linkage is to alternate amino acids or wherein oxidation of the alcohol to the keto form at positions 3, 7 and 12, can also be substituted. Indeed, some of these modifications may occur at various levels in the bile of some species. The derivatives above are generally found as the sodium salts in bile, but, of course, alternate biologically compatible cations could also be substituted, for example, potassium ion, calcium ion, magnesium ion, and the like.

A series of U.S. Pat. Nos.: 2,230,240, issued 18 Jan. 1966; 3,867,413, issued 18 Feb. 1975; 4,100,276, issued 11 July 1978; and 4,119,717, issued 10 Oct. 1978, describe the synthesis of the fusidates and their derivatives; U.S. Pat. No. 4,548,992 and U.S. Pat. No. 4,746,508, also cited below, describe additional derivatives. The fusidates are similar in structure to the cholic acids with similar variations in oxidation state, and the ability to form peptide linkages to various amino acids or peptides through a carboxyl group. The fusidates are derivatives of fusidic acid:

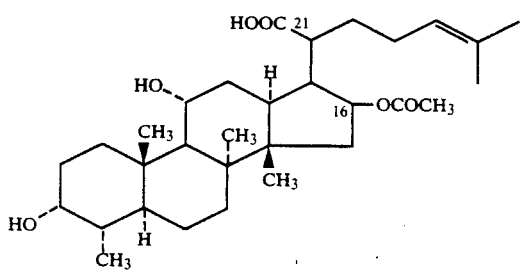

It is seen that the fusidates and their derivatives differ from cholic acid in several respects, including in the length of the side chain at position 17 and in the position of the carboxyl group on the side chain. Importantly, as disclosed in the above-cited patents, these compounds can conveniently be derivatized through position 21 to a variety of substituents. The disclosures of these patents are incorporated herein by reference. It should be further noted that certain of the cephalosporins are, in fact, fusidate derivatives, and these are specifically included within the scope of this term. Illustrative of the cephalosporins which can be employed in the compositions of the invention are cephalosporins $P_1$, $P_2$, $P_3$, $P_4$, and $P_5$ and derivatives thereof.

The use of fusidates as carriers for transmucosal membrane drug delivery has also been disclosed in U.S. Pat. No. 4,548,992 and U.S. Pat. No. 4,746,508, the disclosures of which are incorporated herein by reference. As is the case with regard to the bile acid derivatives, derivatization through the carboxyl group to obtain an amide is preferably with glycine or taurine, other amino acid or peptide, and a variety of salts is available. And, as was the case with bile acid derivatives, various oxidation states of the steroid nucleus are included.

A preferred class of fusidates for use in the invention is that disclosed in U.S. Pat. No. 4,746,508 having the formula:

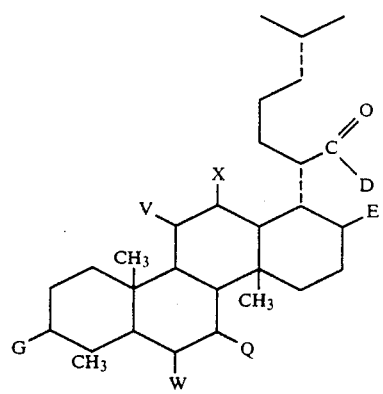

wherein each dashed line, independently, represents a single or double bond; D is a group having a molecular weight below about 600 daltons which renders an effective amount of the compound water-soluble within a range of about pH2 to pH12; E and G each represent OAc, OH, a lower alkyl group or a lower heteroalkyl group; W represents OAc or H; and Q, V and X each represent H or OH, said fusidate compound containing from two to three polar functions, exclusive of the function represented by D.

Preferred embodiments of the fusidates include sodium tauro-24,25-dihydrofusidate (STDHF) and sodium glyco-24,25-dihydrofusidate (SGDHF).

The nonionic detergent or surfactant component has the general formula $RO(CHR'CH_2O)_nR$ wherein one R is H and the other R represents the radical of a saturated or unsaturated cyclic or acyclic organic alcohol of 6-40 carbons, such as a long-chain alcohol or a sterol. Typical long-chain alcohols include those wherein the radicals are lauryl, stearyl, cetyl, and nonyl; the sterols include cholesterol, lanosterol, or various modifications thereof. R' is H or methyl. The value of n can be 1-150, but the preferred value is 1-50, preferably 5-30. Copolymers, including block and random copolymers where R' is H in some residues and methyl in others can be used.

British patent No. 2,127,689 describes a general class of nonionic detergents contemplated to be within the scope of the invention herein. As set forth in this granted patent, various nonionic detergents are available under the trade names Solulan (Amerchol), Emalex (KAO Soap), Brij (ICI), and Laureth (Atlas), or Cetomacrogol (Croda). Other examples include nonylphenol PEO compounds, such as Igepols and Tergitols. Exemplified are ethers of cholesterol, lanolin, lauryl alcohol, cetyl alcohol, and so forth. Any pharmaceutically acceptable ethylene oxide or propylene oxide polymer or copolymer esterified to a hydrophobic radical can be used. Especially preferred is Solulan C-24. Solulan C-24 is a trademark for the nonionic detergent polyoxyethylene-24-cholesterol ether. The recognized commercial generic name for this compound, as set forth by the CTFA is choleth-24.

The compositions of the invention are aqueous suspensions of the drug in mixtures of the bile salt/ fusidate component and the nonionic detergent component. The percentage of each carrier component in the mixture is generally three percent or less, but the total carrier concentration must be a value higher than the critical micellar concentration (CMC) for the components taken together in the mixture. The CMC is the minimum concentration required in order for the component(s) to form micelles in the aqueous medium, as opposed to behavior as individual molecules. The value of the CMC will vary with temperature, pH and ratio of the surfactants; the concentration must be adjusted according to the conditions of dispersion.

The CMC is not a single value, but a range of concentrations. Because the range is relatively narrow, a single concentration within this transition zone is defined as the CMC. The CMC for each individual molecule and for each mixture can be determined experimentally in variety of ways; that illustrated below is the rhodamine 6G method of Carey, M.C., et al *J Colloid Interface Sci* (1969) 31:382-396. In this method, a low concentration of rhodamine 6G is added as a probe in a series of dispersions or solutions of the material to be tested. Where the solute concentration is below the CMC the probe molecule has a lambda$_{max}$ at 523 nm; above the CMC, the probe binds to the micelle, which causes the lambda$_{max}$ to increase to approximately 532 nm. By plotting the wavelength of the maximum absorption of the rhodamine 6G probe as a function of concentration of test materials, two lines of differing slopes are obtained which intersect at the CMC. The value of the intersection is then taken as the value of the CMC for the particular dispersion.

When this procedure is conducted for solutions of STDHF, Solulan C-24, or a 1:1 mixture of these materials, the CMC values (as percent w/v) obtained are 0.14% for STDHF; 0.028% for Solulan C-24; and 0.012% for the mixture of the two—i.e., 0.006% STDHF plus 0.006% Solulan C-24. Thus, for the mixture of STDHF and Solulan C-24, the CMC for the mixture is lower than that for either component alone. These values establish minimum concentration levels needed for the invention composition, and also establish that the two components form mixed micelles. If there were two separate populations of micelles, the CMC as measured by the above-described method would be equal to that of Solulan C-24. The existence of mixed micelles can be verified with other data as described below.

When the CMC is expressed on a molar basis rather than percent w/v, that for STDHF is 2.0 mM, for Solulan C-24, 0.19 mM, and for the mixture, 0.13 mM total surfactant, or 0.042 mM C-24 combined with 0.088 mM STDHF.

Quasi-elastic light-scattering data also show that bile salt/fusidate mixtures with nonionic detergents, which are the excipients herein, form mixed micelles at the concentrations convenient for administration. Solulan C-24 forms micelles with a radius of 75 angstroms; STDHF forms micelles with a radius of 17 angstroms, and the mixture (1:1 w/w) forms micelles with a radius of 40 angstroms.

The pharmaceutical compositions of the invention exhibit low toxicity and efficient permeation. The permeation ability is measured with respect to a mucosal surface such as the nasal, digestive tract, or vaginal surface. This is to be distinguished from transdermal drug delivery, as the drug needs in that case to penetrate the skin. The membrane barrier involved in transmucosal delivery is not equivalent. While applicants are not to be bound by any theory, it is thought that micelles formed by the carrier are able to form pores in the mucosal surface to transport the active ingredient, without destroying the mucosa and it is desirable that this be a reversible effect. Permanent destruction of the membrane per se would be an undesirable and negative side effect of membrane penetration.

While the nasal, vaginal, and digestive tract surfaces are the most commonly used, suitable membranes are also found in the ear, urinary tract, pulmonary system, and areas of the skin surface which are not completely closed such as the gluteal cleft, tymphanic membrane, the crevices between the toes, and the groin. While the compositions of the invention are not intended for transdermal transport per se, penetration of the skin may be enhanced by the disclosed carriers.

The concentration of the carrier is determined not only with regard to the CMC, but also with regard to the degree of penetration needed for the transport of the particular drug. This will vary with the drug characteristics, for example hydrophilicity, amphiphilicity, charge, molecular weight and so forth. The carrier and drug are provided in aqueous buffer. Generally the carrier is mixed with the buffer, and then added to and mixed with the drug, although alternate formulation protocols can be used. While the concentration limits are variable as described above, the excipient aqueous solutiongenerally contains about 0.1%-2.5% v/v of the steroid and detergent, taken together; higher percentages, up to about 6% can be used in some cases. Physiologically acceptable buffers include sodium phosphate buffer, pH 4-10, preferably 5-8, optionally with a suitable concentration of NaCl or other salt—e.g., about 0.01-3 M, preferably 0.05 M-0.6 M.

The concentration of the drug is in an amount effective to treat or prevent a disorder or to regulate a physiological condition in an animal or human, and is variable depending on the dosage required to obtain the desired effect and on the effectiveness of penetration. The concentration and amount of drug administered will depend on the precise parameters determined for the drug in question when administered by the method described. The requirements may vary from those obtained when other modes of administration are used. The composition may, of course, also contain other nontoxic acceptable substances such as preservatives or stabilizing agents.

Administration is by means generally known in the art, most preferably sprays, but also including emulsions, drops, suppositories, lotions, ointments and dry powder aerosols. Slow release formulations, typically containing the composition in microcarriers or polymeric membranes may also be used.

For the administration of dry powder aerosol, a solid drug formulation is prepared by first making a solution containing both the carrier molecules and drug as described above for the aqueous composition. This solution is then lyophilized to obtain a solid drug formulation which is then resuspended in a Freon ® propellant and delivered by standard methods known in the art.

EXAMPLES

The following examples are intended to illustrate but not to limit the invention.

EXAMPLE 1

Comparative Safety of Excipients

Solulan C-24, STDHF, and mixtures thereof were tested with regard to their effect on rat mucosal surfaces as follows.

Male Sprague-Dawley rats weighing between 240-260 g were injected intraperitoneally with sodium pentobarbital (65 mg/kg) to induce anesthesia.

Nasal membrane damage was evaluated as follows: Polyethylene tubing PE-200 and PE-90 were inserted into the trachea and nasal pharynx respectively to allow for the delivery of solutions into the nasal cavity via the nasopharyngeal opening. One ml of solution was delivered to the nasal cavity through the PE-90 tubing at a rate of 1 ml per min; the volume of the nasal cavity is approximately 200 ul. The excess solution flowed out of the nares. After a period of 5, 10 or 15 min the nasal cavity was perfused with 0.9% NaCl at 1 ml/min for 5 min, followed by 2% glutaraldehyde in 100 mM sodium phosphate buffer, pH 7.4. The maxillo- and naso-turbinates were excised for examination by scanning electron microscopy. The resulting photomicrographs were used to evaluate the effect of the test solution on mucosal surface integrity and ciliary morphology; cilia loss is considered by some to be one of the mildest forms of damage to the respiratory epithelium.

The micrographs were rated on a scale of 1-5 representing "normal" to "gross abnormalities". The results are shown in FIGS. 1 and 2. FIG. 1 shows the results with respect to mucosal surface integrity of a 5-min exposure to either Solulan C-24 alone, to STDHF alone, or to mixtures of each. As shown in FIG. 1, the deleterious effects of C-24 and STDHF were not additive; alteration in the membrane due to the mixture of 0.5% of each was less than that observed when a solution of 0.5% of STDHF was applied alone. Similar results were obtained with regard to ciliary morphology, as shown in FIG. 2, where the combination of Solulan C-24 and STDHF was less destructive than STDHF alone.

Consistent results were obtained when red blood cell (RBC) lysis was evaluated as a measure of toxicity and SGDHF was used as the fusidate component. As shown in FIG. 3, Solulan C-24 alone showed low values of RBC lysis over a concentration range of 0-0.3%; SGDHF gave 100% lysis at 0.3% concentration. However, addition of 0.2% or more Solulan C-24 to 0.3% or 0.5% SGDHF significantly reduced RBC lysis. Thus, the addition of the detergent appears to protect against the lytic effect of the fusidate.

EXAMPLE 2

Permeation Enhancing Ability

Efficacy in transport of insulin and of human growth hormone across rat nasal tissue was evaluated. Male Sprague-Dawley rats (Simonsen, Gilroy, CA, 240-300 gm) were anesthetized by subcutaneous injection of Acepromazine (3 mg/kg) followed 10 minutes later by intraperitoneal injections of inactin (100 mg/kg) for experiments shown in FIGS. 4-6 or by intraperitoneal (IP) injection of sodium pentobarbital (65 mg/kg), with additional doses given intravenously as necessary for experiments shown in FIGS. 7-8. A trachea tube was inserted to assist breathing.

In FIGS. 4-6, insulin or hGH was delivered directly via the nares; no esophageal cannula was inserted; the test solution (50 ul) was delivered 1 cm into the nasal cavity using PE 10 tubing attached to a Hamilton syringe.

In FIGS. 7-8, for delivery to the nasal cavity, a 5 cm cannula was inserted through the esophagus and through the nasopharyngeal opening and tied in place, leaving approximately 2.5 cm of the cannula exposed. For intranasal delivery, 80 ul of the test solution containing insulin or hGH was drawn up in a 100 ul Hamilton syringe, a 5 cm piece of PE 10 tubing was attached to the syringe, the tubing was inserted completely into the esophageal cannula so that the end was even with the end of the guide cannula, and the test solution was injected.

In all cases, blood samples (0.5 ml) were drawn from a catheter in the right jugular vein and diluted with heparinized saline. Plasma (300-400 ul) was separated and stored at 4° C. for less than 48 hours prior to analysis of growth hormone using an immunoradiometric assay (Tandem R, Hybritech, Inc, San Diego, Calif.) or of insulin using a radioimmunoassay (Micromedic, ICN Micromedic Systems, Horsham, Pa.). Plasma insulin or hGH concentrations were corrected for the dilution with heparinized saline. Estimations of area under the curve (AUC) of plots of plasma insulin or hGH concentration versus time were calculated using the trapezoidal rule. The results are shown in FIGS. 4-8.

FIG. 4 shows the results of administration of 5IU/kg insulin at various concentrations of STDHF alone and in admixture with Solulan C-24. As shown in the figure, the most effective transport of insulin occurred at mixtures of 0.5% of each. The effect of permeation was considerably greater than for either 0.5% or 1% STDHF or 0.5% or 1% C-24 alone; in fact the mixture of 0.5% each STDHF and C-24 was more than additive of that for each separately, and more than additive even of that for 1% of each separately. The superior results of the mixture cannot, it is clear, be accounted for simply by an increase in excipient concentration from 0.5% to 1%.

FIG. 5 shows the time course of these results, with the results shown as micro-Units of insulin per ml of plasma. As shown in the figure, a high level of insulin could be maintained with the 0.5%/0.5% mixture. Compositions with STDHF or Solulan C-24 alone gave lower levels, and the levels obtained with the mixture were greater than would be expected if the levels were additive.

FIG. 6 shows analogous results for nasal delivery of 3 mg/kg human growth hormone, where, again, mixtures containing 0.5% of each component showed a higher transfer for hGH than compositions containing 0.5% of either alone.

FIG. 7 shows analogous results for 0.3 mg/kg hGH delivered intranasally using mixtures of the bile salt sodium glycocholate in admixture with Solulan C-24. In this case, mixtures containing 0.3% of each component appeared to be the most effective; at a higher concentration level, 0.5% of each, the mixture gave lowered absorption.

FIG. 8 shows the time course of hGH levels in plasma. The curve of solid triangles represents the 0.3% glycocholate/0.3% Solulan C-24 combination, which indicates that the initial rise in ng hGH per ml plasma is better than that for 0.3 or 0.5% glycocholate alone or 0.3% C-24 alone. Also, the elevated levels are maintained for a longer time period. Higher concentrations of the mixture were not tested in this experiment.

EXAMPLE 3

Typical Formulations

The following are illustrative compositions included within the invention.

In this example, "PEO" represents polyethylene oxide and the number following it, the number of units; PPO represents polypropylene oxide with the number following representing the number of units. Additional components include buffers and preservatives.

A. A carrier composition containing 0.5% STDHF +0.5% lanosterol PEO-28 ether is prepared. To this vehicle is added the indicated amount of active ingredient to prepare the following compositions:

| A.1. | 0.05 mg/ml insulin; |
|---|---|
| A.2. | 18 mg/ml human growth hormone; |
| A.3. | 4 mg/ml LHRH; |
| A.4. | 1 mg/ml calcitonin; |
| A.5. | 0.1 mg/ml TSH. |

B. A carrier mixture containing 0.3% sodium glycocholate plus 0.25% nonyl-PEO-11 is prepared. To this carrier preparation is added the indicated amount of active ingredient to prepare the following compositions:

| B.1. | 0.1 mg/ml insulin; |
|---|---|
| B.2. | 35 mg/ml human growth hormone; |
| B.3. | 2 mg/ml LHRH; |
| B.4. | 0.25 mg/ml calcitonin; |
| B.5. | 0.25 mg/ml TSH. |

C. A carrier preparation containing 0.4% of a lysine derivative of fusidic acid along with 0.2% cetyl-PPO-5 is prepared. To this mixture is added the indicated amount of active ingredient to prepare the following compositions:

| C.1. | 0.2 mg/ml insulin; |
|---|---|
| C.2. | 25 mg/ml human growth hormone; |
| C.3. | 8 mg/ml LHRH; |
| C.4. | 0.5 mg/ml calcitonin; |
| C.5. | 0.5 mg/ml TSH. |

We claim:

1. An aqueous composition for transmucosal membrane administration of a drug which composition comprises an aqueous physiologically compatible buffer which contains:
   (a) an amount of drug effective to affect the condition to which it is directed,
   (b) at least one nonionic detergent of the formula RO(CHR'CH$_2$O)$_n$R, wherein R' is H or methyl, n is an integer of 1–150; and one R is H and the other R is an organic residue selected from saturated or unsaturated acyclic or cyclic radicals of 6–40 C; and
   (c) at least one bile salt or fusidate or derivative thereof; wherein
      (i) the weight ratio of detergent of (b) to the bile salt/fusidate/derivative of (c) is 1:10–10:1, and
      (ii) the concentration of detergent of (b) plus bile salt/fusidate/derivative of (c) is higher than the critical micellar concentration (CMC) of the mixture of these components, and wherein
      (iii) the detergent of (b) and bile salt/fusidate/derivative of (c) are present in the composition as mixed micelles.

2. The composition of claim 1 wherein the drug is a peptide/protein drug.

3. The composition of claim 2 wherein the peptide/protein drug is selected from the group consisting of insulin, human growth hormone, atrial natriuretic factor, and calcitonin.

4. The composition of claim 1 wherein n is 1–50.

5. The composition of claim 1 wherein R' is H.

6. The composition of claim 1 wherein the non-H R is the organic radical of a sterol.

7. The composition of claim 1 wherein the non-H R is the organic radical of nonyl, cetyl or lauryl alcohol.

8. The composition of claim 1 wherein the nonionic detergent is choleth-24.

9. The composition of claim 1 wherein the bile salt, fusidate or derivative is selected from STDHF, SGDHF, and sodium glycocholate.

10. The composition of claim 1 wherein the bile salt or fusidate is STDHF and the nonionic detergent is choleth-24.

11. A composition for transmucosal membrane administration of a drug which composition comprises the composition of claim 1 in lyophilized form.

12. A method to treat, prevent, or regulate a condition responsive to a drug which method comprises contacting a mucosal membrane of a subject in need of such treatment, prevention or regulation with a composition which comprises an aqueous composition for the transmucosal membrane administration of a drug which composition comprises:
   (a) an amount of drug effective to treat, prevent or regulate the condition to which it is directed,
   (b) at least one nonionic detergent of the formula RO(CHR'CH$_2$O)$_n$R, wherein R' is H or methyl, n is an integer of 1–150; and one R is H and the other R is an organic residue selected from saturated or unsaturated acyclic or cyclic radicals of 6–40 C; and
   (c) at least one bile salt or fusidate or derivative thereof; wherein
      (i) the weight ratio of detergent of (b) to the bile salt/fusidate/derivative of (c) is 1:10–10:1, and
      (ii) the concentration of detergent of (b) plus bile salt/fusidate/derivative of (c) is higher than the critical micellar concentration (CMC) of the mixture of these components, and wherein
      (iii) the detergent of (b) and bile salt/fusidate/derivative of (c) are present in the composition as mixed micelles.

13. The method of claim 12 wherein the drug is a peptide/protein drug.

14. The method of claim 12 wherein the peptide/protein drug is selected from the group consisting of insulin, human growth hormone, atrial natriuretic factor, and calcitonin.

15. The method of claim 12 wherein the membrane contacted is selected from the pulmonary, rectal, vaginal, occular, and nasal membranes.

16. The method of claim 12 wherein the composition is administered as a spray.

17. The method of claim 12 wherein R' is H.

18. The method of claim 12 wherein n is 1–50.

19. The method of claim 12 wherein the non-H R is the radical of nonyl, cetyl or lauryl alcohol or a sterol.

20. The method of claim 12 wherein the nonionic detergent is choleth-24.

21. The method of claim 12 wherein the bile salt, fusidate or derivative is selected from STDHF, SGDHF and sodium glycocholate.

22. The method of claim 12 wherein the bile salt, fusidate or derivative is STDHF and the nonionic detergent is choleth-24.

23. A method to treat, prevent, or regulate a condition responsive to a drug which method comprises contacting a mucosal membrane of a subject in need of such treatment, prevention or regulation with a composition which comprises the composition of claim 1 in lyophilized form.

* * * * *